United States Patent [19]

Yuan et al.

[11] Patent Number: 5,616,142
[45] Date of Patent: Apr. 1, 1997

[54] VERTEBRAL AUXILIARY FIXATION DEVICE

[76] Inventors: Hansen A. Yuan, 5066 Pine Valley Dr., Fayetteville, N.Y. 13064; Chih-I Lin, 14292 Spring Vista La., Chino Hills, Calif. 91709

[21] Appl. No.: 277,764

[22] Filed: Jul. 20, 1994

[51] Int. Cl.$^6$ ............ A61B 17/70; A61B 17/80
[52] U.S. Cl. ............ 606/61; 606/71; 403/340
[58] Field of Search ............ 606/69, 70, 71, 606/60, 61, 72, 77; 403/339, 340, 331

[56] References Cited

U.S. PATENT DOCUMENTS

| | | | |
|---|---|---|---|
| 2,406,832 | 9/1946 | Hardinge | 606/71 |
| 2,486,303 | 10/1949 | Longfellow | 606/71 |
| 4,246,660 | 1/1981 | Wevers | 606/71 |
| 5,108,399 | 4/1992 | Eitenmuller et al. | 606/77 |

FOREIGN PATENT DOCUMENTS

| | | | |
|---|---|---|---|
| 2808971 | 9/1979 | Germany | 606/71 |
| 779411 | 7/1957 | United Kingdom | 403/331 |

*Primary Examiner*—Tamara L. Graysay
*Attorney, Agent, or Firm*—Bacon & Thomas

[57] ABSTRACT

A vertebral auxiliary fixation device comprises a receiving piece, a sliding piece, and a plurality of fastening elements. The receiving piece is provided with two sliding grooves in which the sliding piece is slidably received. The receiving piece and the sliding piece are provided respectively with through holes engageable with the fastening elements which are fastened onto a vertebra intended to be fixed.

9 Claims, 3 Drawing Sheets

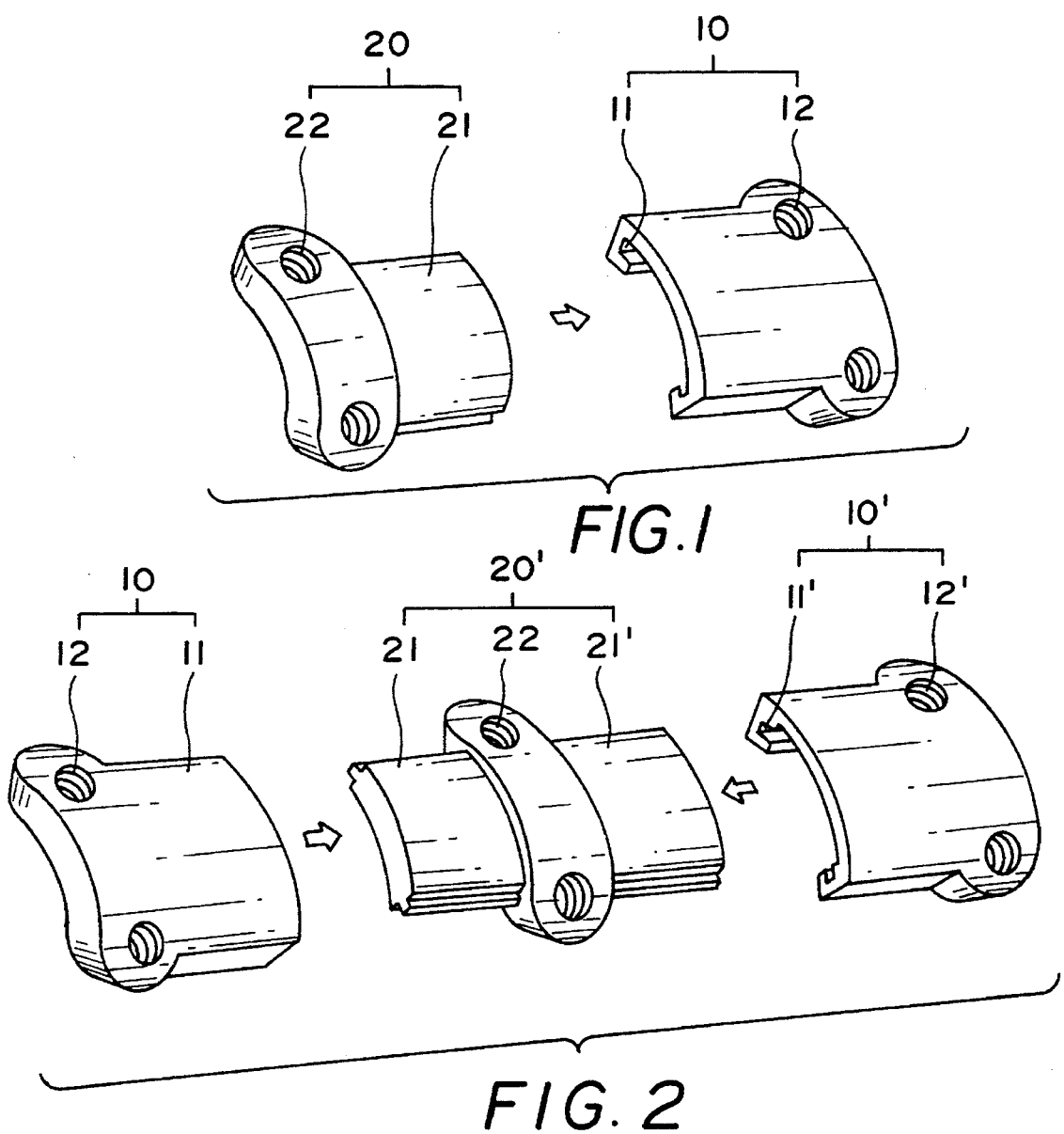
FIG. 1
FIG. 2
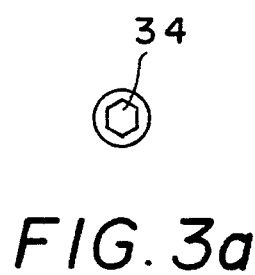
FIG. 3a
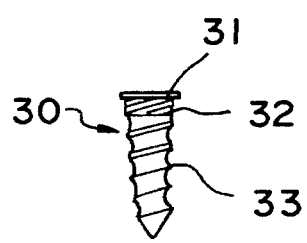
FIG. 3b

VERTEBRAL AUXILIARY FIXATION DEVICE

FIELD OF THE INVENTION

The present invention relates generally to a vertebral fixation device, and more particularly to a vertebral auxiliary fixation device.

BACKGROUND OF THE INVENTION

According to the conventional surgical operation for fixing and retrieving a deformed or injured vertebra, it is a common surgical practice that a foreign object such as a bone graft, or a filling material such as a hydroxylapitite, is implanted into the vertebra or between the vertebrae. However, the patient under treatment is rather susceptible to a severe pain caused by the implanted foreign object or filling material which is jutted out to touch the nerve or to injure the tissues contiguous to the vertebra under treatment. It is therefore necessary that a precautionary measure is taken to prevent the implanted foreign object or filling material from bulging out of the vertebra or from bulging out between the vertebrae. A bone plate is generally used as a means for preventing the implanted foreign object from jutting out; nevertheless the bone plate which covers the implanted foreign object can hinder the surgical operation. In addition, the implanted foreign object is even vulnerable to falling in view of the fact that the bone plate can not be fastened intimately with the vertebra intended to be fixed and that the bone screws can become loosened easily.

SUMMARY OF THE INVENTION

It is therefore the primary objective of the present invention to provide a vertebral auxiliary fixation device having the effect of holding a foreign object which is implanted in a vertebra to be fixed or is implanted between the vertebrae to be fixed.

It is another objective of the present invention to provide a vertebral auxiliary fixation device which is made up of a receiving piece, and a sliding piece having a tongue. The receiving piece is provided with a plurality of through holes and with two sliding grooves in which the tongue of the sliding piece is slidably received. The sliding piece is also provided with a plurality of through holes similar in construction to the through holes of the receiving piece. The through holes of the receiving piece and the sliding piece are engageable with a plurality of fastening elements, which are fastened onto a vertebra intended to be fixed.

The receiving piece and the sliding piece may be made of any orthopedic material capable of being readily assimilated by the tissues of a human body, such as a material that is used in making the synthetic ligament.

The receiving piece may be of any shape, preferably a rectangular shape or a shape similar to the rectangular shape. The two sliding grooves of the receiving piece may be of any construction, preferably the two sliding grooves being located at the lateral sides of the receiving piece and facing each other.

The sliding piece is shaped and sized in accordance with the shape and the size of the receiving piece such that the tongue of the sliding piece can be slidably fitted into the sliding grooves of the receiving piece.

If necessary, the sliding piece and the receiving piece may be fastened together fixedly after the sliding piece is fitted into the receiving piece.

The present invention may be modified in such a manner that the sliding piece and the receiving piece both have a tongue and two sliding grooves, in which the tongue and the sliding grooves are so juxtaposed that the tongue of said sliding piece is slidably received in the sliding grooves of the receiving piece while the tongue of said receiving piece is slidably received in the sliding grooves of the sliding piece.

Similarly, the receiving pieces of the present invention may be further modified to have two juxtaposed sets of two sliding grooves, and the sliding piece of the present invention has two juxtaposed tongues which are able to be slidably received in the two juxtaposed sets of two sliding grooves, respectively.

When the present invention is used in a surgical operation in which an intervertebral disk is implanted, a single sliding piece and a single receiving piece may be fastened together in order to prevent the intervertebral disk from jutting out to hurt the tissues contiguous to the vertebra under treatment. However, a plurality of the receiving pieces and a plurality of the sliding pieces may be used in a surgical operation in which two or more intervertebral disks are to be implanted. In order to enhance the effect of holding the implanted foreign objects, it is suggested that two receiving pieces, two sliding pieces, or one receiving piece and one sliding piece located in the middle vertebra are united to a compound receiving/sliding piece, each end of which is made up of the two sliding grooves or the tongue, or one end of which is made up of the two sliding grooves while another end of which is made up of the tongue. Let's take three vertebrae as an example for illustration. In such a case, two sets of the vertebra auxiliary fixation devices of the present invention should be employed. The arrangements must be made from the anterior to the posterior in accordance with the following three sequences: the receiving piece, the sliding piece, the receiving piece, and the sliding piece; the receiving piece, the sliding piece, the sliding piece, and the receiving piece; or the sliding piece, the receiving piece, the receiving piece, the sliding piece. According to the first sequence described above, the sliding piece and the receiving piece, which are located in the middle, are united to one sliding-receiving piece, such that one end is made up of the two sliding grooves and another end is made up of the tongue. According to the second sequence mentioned above, two sliding pieces located in the middle are joined together to form a sliding-sliding piece. According to the third sequence mentioned above, two receiving pieces located in the middle are joined together to form a receiving-receiving piece. Such forms of combination as described above are summed up as the compound receiving/sliding piece.

The through holes of the receiving piece and the sliding piece are not specifically located; nevertheless they are preferably located at another end of the sliding grooves and tongue portion. In case of the compound receiving/sliding piece, the through holes may be located at both sides of the middle portion of the compound sliding/receiving piece.

In order to improve the effect of fastening the receiving piece and the sliding piece together, the coupling edges of the sliding grooves of the receiving piece and the tongue of the sliding piece may be serrated so that the receiving piece can be clamped securely after the receiving piece and the sliding piece are coupled together.

The fastening elements used in the present invention are similar in construction to the conventional fastening means such as screws, preferably the double-threaded self-locking screws which are disclosed by this inventor of the present invention in the pending U.S. patent application (Ser. No.08/

249,341, filing date 27 May 1994, now abandoned). The double-threaded self-locking screw is characterized in that it is provided with a nail portion having thereon a thread for fastening onto a vertebra intended to be fixed, and that it is provided with a plurality of intertwined threads contiguous to the threaded heads and engageable with the corresponding threaded through hole of the receiving piece and the sliding piece, each of which has a pitch equal to that of the thread on the nail portion.

If the conventional screw is used, it is suggested that the receiving piece and/or the sliding piece is provided at the side of the through hole thereof with a retaining tenon, which serves to urge the screw after the screw has been tightened. In other words, the retaining tenon serves to prevent the screw from becoming loosened.

The receiving piece, the sliding piece and the fastening elements of the present invention are made of a material similar to the material which is used in making an artificial ligament and which can be assimilated by the tissues of the human body. According to the present invention, no additional auxiliary fixation device is required for preventing the implanted foreign object from jutting out of the fixed vertebra in view of the fact that the implanted foreign object has been readily fused with the fixed vertebra several months after the surgical operation. In the meantime, the receiving piece, the sliding piece and the fastening elements of the present invention have also been readily assimilated by the tissues of the human body, thereby resulting in little or no foreign object left in the human body. As a result, the risk that the implanted foreign object may bring about an unwanted side effect in the human body is greatly minimized.

The foregoing objectives, features and functions of the present invention will be more readily understood upon a thoughtful deliberation of the following detailed description of the embodiments of the present invention in conjunction with the accompanying drawings.

BRIEF DESCRIPTION OF THE DRAWINGS

FIG. 1 shows an exploded view of a first preferred embodiment of the present invention.

FIG. 2 shows an exploded view of a second preferred embodiment of the present invention.

FIGS. 3a and 3b show a preferred embodiment of the fastening element of the present invention.

DETAILED DESCRIPTION OF THE INVENTION

Figure 4A:
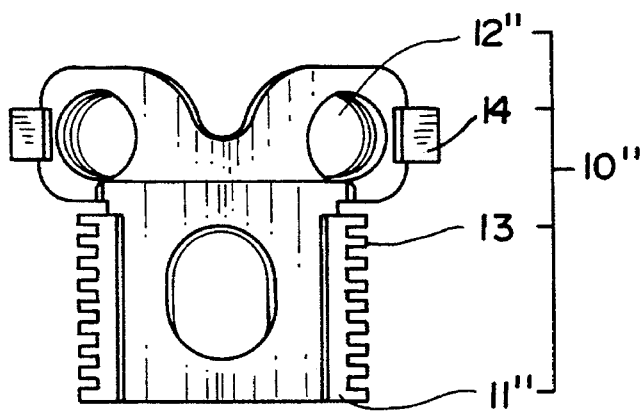
FIGS. 4a and 4b how respectively a top plan view of a receiving piece and a sliding piece in accordance with another preferred embodiment of the present invention.

As shown in FIG. 1, the present invention comprises a receiving piece 10, and a sliding piece 20. The receiving piece 10 is provided with two grooves 11 and two threaded through holes 12 engageable with two fastening elements (not shown in the drawing). The sliding piece 20 is provided with a tongue-shaped sliding portion 21 and two threaded through holes 22 engageable with two fastening elements (not shown in the drawing).

A compound receiving/sliding piece 20' is shown in FIG. 2 in which two identical receiving pieces 10, 10' are provided respectively with sliding grooves 11, 11' and through holes 12, 12'; and the compound receiving/sliding piece 20' is provided at each end thereof with a tongue-shaped sliding portion 21(21') and at each side of the middle portion with one through hole 22.

As shown in FIG. 3, a double-threaded screw 30 is used for fastening the receiving piece or the sliding piece onto a vertebra intended to be fixed, which comprises a head 31 having therein a tool hole 34, a plurality of intertwined threads 32 adjacent to the head 31 and engageable with the through holes of the receiving piece or the sliding piece, and a thread 33 for fastening onto a vertebra to be fixed, in which each of the intertwined threads 32 has a pitch equal to that of the thread 33.

Figure 4B:
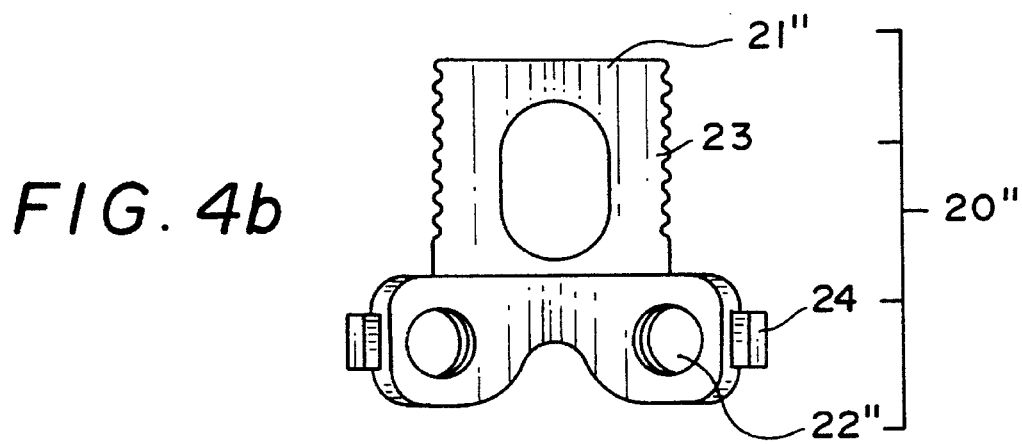
Figure 4C:
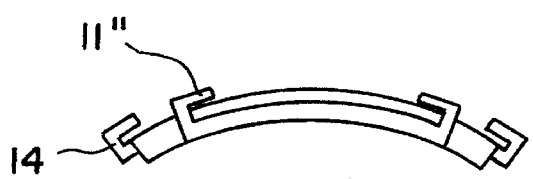
FIG. 4c shows a side elevational view of the receiving piece in FIG. 4-1.
Figure 4D:
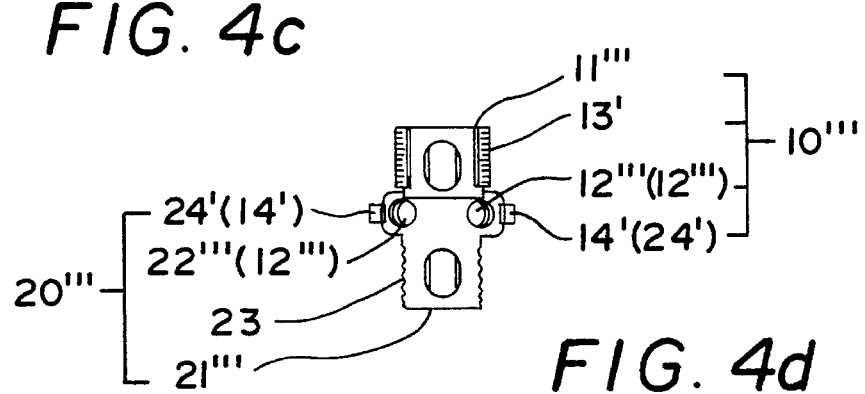
FIG. 4d shows a top plan view of a compound receiving/sliding piece combining the receiving piece and the sliding piece shown in FIGS. 4-1 and 4-2.

Another embodiment of the present invention is illustrated in FIGS. 4a, 4b and 4c, in which the reference numerals of 10", 11", 12", 20", 21" and 22" are similar in definition to the like reference numerals of FIG. 1. The groove 11" of the sliding piece 10" is provided with a serrated groove tenon 13 while the tongue-shaped sliding portion of the sliding piece 20" is provided with a toothed tenon 23. The through holes 12" and 22" are provided respectively and contiguously with retaining tenons 14 and 24. A compound receiving/sliding piece having the serrated groove tenon and the retaining tenon is shown in FIG. 4d, in which the reference numerals of 10'"–14'" and 20'"–24'" are similar in definition to the like numerals of FIGS. 4a and 4b.

Figure 5:
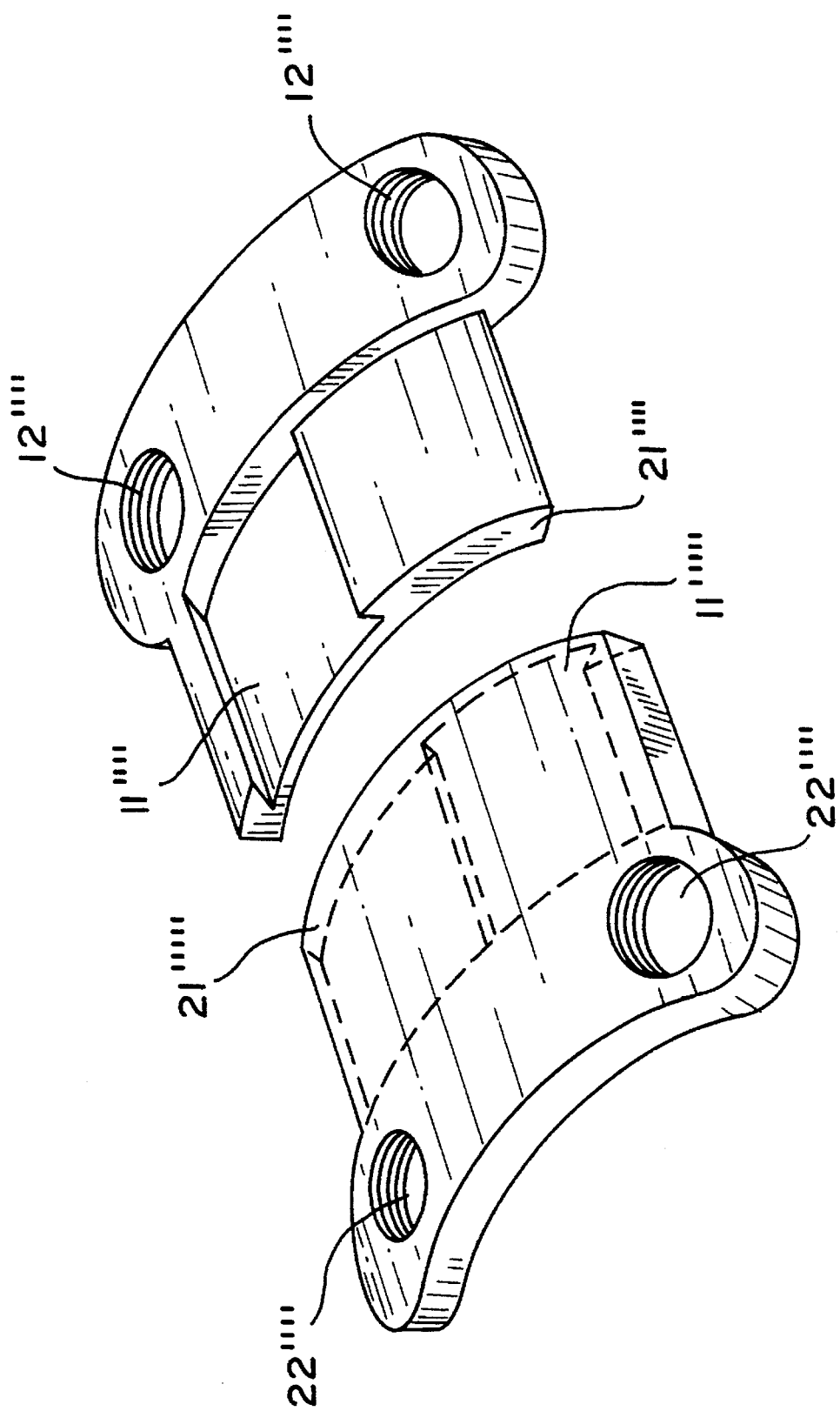
FIG. 5 shows a perspective view of a set of two juxtaposed receiving/sliding pieces according to still another preferred embodiment of the present invention.

One set of two juxtaposed receiving/sliding pieces are shown side by side in FIG. 5. The first juxtaposed receiving/sliding piece has two receiving grooves 11"" and a tongue-shaped sliding portion 21"" while the second set of the juxtaposed receiving/sliding piece has two receiving grooves 11""' and a tongue-shaped sliding portion 21""'. The juxtaposed receiving/sliding pieces are provided respectively with through holes 12"" and 22"".

What is claimed is:

1. A vertebral auxiliary fixation device comprising:

a receiving piece having two sliding grooves and a plurality of through holes adapted to engage with a plurality of fastening elements for fastening onto a vertebra intended to be fixed;

a sliding piece having a first tongue-shaped sliding portion slidably received in said sliding grooves of said receiving piece and having a plurality of through holes adapted to engage with a plurality of fastening elements for fastening onto a vertebra intended to be fixed, both said receiving piece and said sliding piece being made of an orthopedic material that is readily assimilated by tissues of a human body; and a second receiving piece including a second receiving portion provided with two sliding grooves and a plurality of through holes spaced from said second receiving portion, said sliding piece actually including said first and a second tongue-shaped sliding portions which extend in opposite directions with said plurality of through holes being positioned between said first and second tongue-shaped sliding portions, each of said first and second tongue-shaped sliding portions being adapted to slidably receive a respective one of said receiving pieces.

2. A vertebral auxiliary fixation device comprising:

a receiving piece having two sliding grooves and a plurality of through holes adapted to engage with a plurality of fastening elements for fastening onto a vertebra intended to be fixed; and a sliding piece having a tongue-shaped sliding portion slidably received in said sliding grooves of said receiving piece and having a plurality of through holes adapted to engage with a plurality of fastening elements for fastening onto a vertebra intended to be fixed, both said receiving piece and said sliding piece being made of an orthopedic material that is readily assimilated by tissues of a human body, wherein the sliding portion of said sliding piece is formed with a toothed tenon along opposing lateral sides thereof and the two sliding grooves of said receiving piece are each provided with a serrated groove tenon.

3. The vertebral auxiliary fixation device according to claim 2, further comprising two retaining tenons each of which is attached to one of said receiving piece and said sliding piece directly adjacent said first and second plurality of fastening elements respectively.

4. A vertebral auxiliary fixation device comprising:

a receiving piece having two sliding grooves and a plurality of through holes adapted to engage with a plurality of fastening elements for fastening onto a vertebra intended to be fixed; and a sliding piece having a tongue shaped sliding portion slidably received in said sliding grooves of said receiving piece and having a plurality of through holes adapted to engage with a plurality fastening elements for fastening onto a vertebra intended to be fixed, both said receiving piece and said sliding piece being made of an orthopedic material that is readily assimilated by tissues of a human body, wherein each of said receiving piece and said sliding piece includes respective juxtaposed receiving and sliding portions.

5. A vertebral auxiliary fixation device comprising:

a receiving piece including a receiving portion provided with two sliding grooves and a plurality of through holes, spaced from said receiving portion, that are adapted to engage with a plurality of first fastening elements for fastening said receiving piece onto a vertebra intended to be fixed;

a sliding piece including a first tongue-shaped sliding portion slidably received in the sliding grooves of said receiving piece and a plurality of through holes, spaced from said first tongue-shaped sliding portion, that are adapted to engage with a plurality of second fastening elements for fastening said sliding piece onto a vertebra intended to be fixed, wherein said receiving piece and said sliding piece are directly engaged solely by the slidable interconnection of said first tongue-shaped sliding portion and said receiving portion such that removal of either of said plurality of first fastening elements or said plurality of second fastening elements will permit said receiving piece and said sliding piece to be slidably disengaged; and a second receiving piece including a second receiving portion provided with two sliding grooves and a plurality of through holes spaced from said second receiving portion, said sliding piece actually including said first and a second tongue-shaped sliding portions which extend in opposite directions with said plurality of through holes being positioned between said first and second tongue-shaped sliding portions, each of said first and second tongue shaped sliding portions being adapted to slidably receive a respective one of said receiving pieces.

6. The vertebral auxiliary fixation device according to claim 5, wherein both said receiving piece and said sliding piece are made of an orthopedic material that is readily assimilated by tissues of a human body.

7. A vertebral auxiliary fixation device comprising:

a receiving piece including a receiving portion provided with two sliding grooves and a plurality of through holes, spaced from said receiving portion, that are adapted to engage with a plurality of first fastening elements for fastening said receiving piece onto a vertebra intended to be fixed; and a sliding piece including a tongue-shaped sliding portion slidably received in the sliding grooves of said receiving piece and a plurality of through holes, spaced from said tongue-shaped sliding portion, that are adapted to engage with a plurality of second fastening elements for fastening said sliding piece onto a vertebra intended to be fixed, wherein said receiving piece and said sliding piece are directly engaged solely by the slidable interconnection of said tongue-shaped sliding portion and said receiving portion such that removal of either of said plurality of first fastening elements or said plurality of second fastening elements will permit said receiving piece and said sliding piece to be slidably disengaged wherein the sliding portion of said sliding piece is formed with a toothed tenon along opposing lateral sides thereof and the two sliding grooves of said receiving piece are each provided with a serrated groove tenon.

8. The vertebral auxiliary fixation device according to claim 7, further comprising two retaining tenons each of which is attached to one of said receiving piece and said sliding piece directly adjacent said first and second plurality of fastening elements respectively.

9. A vertebral auxiliary fixation device comprising:

a receiving piece including a receiving portion provided with two sliding grooves and a plurality of through holes, spaced from said receiving portion, that are adapted to engage with a plurality of first fastening elements for fastening said receiving piece onto a vertebra intended to be fixed; and a sliding piece including a tongue-shaped sliding portion slidably received in the sliding grooves of said receiving piece and a plurality of through holes, spaced from said tongue-shaped sliding portion, that are adapted to engage with a plurality of second fastening elements for fastening said sliding piece onto a vertebra intended to be fixed, wherein said receiving piece and said sliding piece are directly engaged solely by the slidable interconnection of said tongue-shaped slidling portion and said receiving portion such that removal of either said plurality of first fastening elements or said plurality of second fastening elements will permit said receiving piece and said sliding piece to be slidably disengaged, wherein each of said receiving piece and said sliding piece includes respective juxtaposed receiving and sliding portions.

* * * * *